US012734240B1

(12) United States Patent
Temnik et al.

(10) Patent No.: US 12,734,240 B1
(45) Date of Patent: Sep. 15, 2026

(54) PHARMACEUTICAL COMPOSITION AND METHOD OF TREATING HEMATOLOGIC MALIGNANCIES

(71) Applicant: ISM BIOSCIENCES LLC, Miami, FL (US)

(72) Inventors: Max Temnik, Miami, FL (US); Victor Gurin, Richmond, VA (US); Sergey Gurin, Richmond, VA (US)

(73) Assignee: ISM BIOSCIENCES LLC, Miami, FL (US)

( * ) Notice: Subject to any disclaimer, the term of this patent is extended or adjusted under 35 U.S.C. 154(b) by 0 days.

(21) Appl. No.: 19/076,021

(22) Filed: Mar. 11, 2025

(51) Int. Cl.
*A61K 47/54* (2017.01)
*A61K 33/30* (2006.01)
*A61P 35/02* (2006.01)

(52) U.S. Cl.
CPC ............ *A61K 47/547* (2017.08); *A61K 33/30* (2013.01); *A61P 35/02* (2018.01)

(58) Field of Classification Search
CPC ........ A61K 47/547; A61K 33/30; A61P 35/02
See application file for complete search history.

(56) References Cited

U.S. PATENT DOCUMENTS

| | | | |
|---|---|---|---|
| 8,491,938 | B2 | 7/2013 | Feng |
| 9,861,659 | B2 | 1/2018 | Novak et al. |
| 10,183,041 | B2 | 1/2019 | Novak et al. |
| 10,221,133 | B2 | 3/2019 | Augeri et al. |
| 10,226,484 | B2 | 3/2019 | Novak et al. |
| 10,799,530 | B1 | 10/2020 | Novak et al. |
| 10,857,180 | B2 | 12/2020 | Novak et al. |
| 10,933,091 | B1 | 3/2021 | Novak et al. |
| 11,286,236 | B2 | 3/2022 | Novak et al. |
| 11,433,095 | B1 | 9/2022 | Novak et al. |
| 11,484,550 | B2 | 11/2022 | Novak et al. |
| 11,484,610 | B2 | 11/2022 | Novak et al. |
| 11,504,346 | B2 | 11/2022 | Tomat et al. |
| 11,596,650 | B2 | 3/2023 | Novak et al. |
| 11,638,721 | B2 | 5/2023 | Novak et al. |
| 11,730,835 | B2 | 8/2023 | Novak et al. |
| 11,779,597 | B2 | 10/2023 | Novak et al. |
| 11,827,588 | B2 | 11/2023 | Novak et al. |
| 11,865,184 | B2 | 1/2024 | Krizhanovsky et al. |
| 11,896,610 | B2 | 2/2024 | Novak et al. |
| 11,944,640 | B2 | 4/2024 | Chung |
| 11,986,541 | B2 | 5/2024 | Novak et al. |
| 12,011,458 | B2 | 6/2024 | Novak et al. |
| 12,036,238 | B2 | 7/2024 | Novak et al. |
| 12,037,309 | B2 | 7/2024 | Novak et al. |
| 12,097,215 | B2 | 9/2024 | Novak et al. |
| 12,138,322 | B2 | 11/2024 | Novak et al. |
| 12,233,089 | B2 | 2/2025 | Novak et al. |
| 12,280,065 | B2 | 4/2025 | Kimball et al. |
| 12,344,626 | B2 | 7/2025 | Kimball et al. |
| 2006/0040980 | A1 | 2/2006 | Lind et al. |
| 2010/0172994 | A1 | 7/2010 | Sigmund et al. |
| 2011/0117210 | A1 | 5/2011 | Ugolkov |
| 2021/0187016 | A1 | 6/2021 | Novak et al. |
| 2021/0322467 | A1 | 10/2021 | Novak et al. |
| 2022/0313731 | A1 | 10/2022 | Novak et al. |
| 2023/0061538 | A1 | 3/2023 | Novak et al. |
| 2025/0032538 | A1 | 1/2025 | Novak |
| 2025/0213609 | A1 | 7/2025 | Chung |
| 2025/0375475 | A1 | 12/2025 | Temnik et al. |
| 2026/0029404 | A1 | 1/2026 | Temnik et al. |

FOREIGN PATENT DOCUMENTS

| | | | | |
|---|---|---|---|---|
| GB | 2597446 A | 2/2022 | | |
| KR | 100925516 B1 | 11/2009 | | |
| WO | 2009072120 A1 | 6/2009 | | |
| WO | WO-2021126231 A1 * | 6/2021 | ............ | A61K 33/30 |
| WO | 2022203684 A1 | 9/2022 | | |

OTHER PUBLICATIONS

Novak et al., "In Vitro Anticancer Activity of the Light Stable Zinc Isotope (64Zn) Compounds," Anticancer Research 42, 2002, pp. 5685-5698.

Perez Jesus et al., "Phase 1 First-in-Human Dose escalation and Dose Expansion Stud of KLS-1 (64Zinc Aspartate) in Patients With Cancer and Neurodegenerative Diseases," Curesus, Oct. 4, 2022.

International Search Report and Written Opinion received in PCT/US2026/018394 mailed Jun. 2, 2026, pp. 1-8.

Schilling, Kathrin et all: "Investigations on Zinc Isotope Fractionation in Breast Cancer Tissue Using in vitro Cell Culture Uptake-Efflux Experiments" published on Jan. 20, 2022 in Frontiers in Medicine, https://www.frontiersin.org/articles/10.3389/fmed.2021.746532/full.

Schilling, Kathrin et all: "Zinc stable isotopes in urine as diagnostic for cancer of secretory organs" published on May 12, 2021: https://pubmed.ncbi.nlm.nih.gov/33877364/.

Costello, Leslie et all: "Zinc: The Wonder Drug for the Treatment of Carcinomas" published on Jun. 25, 2020: https://pmc.ncbi.nlm.nih.gov/articles/PMC7316362/.

Hastuti, Agustina et all: "Cu and Zn isotope ratio variations in plasma for survival prediction in hematological malignancy cases" published on Oct. 2, 2020: https://pmc.ncbi.nlm.nih.gov/articles/PMC7532200/.

Zhang, Mengqi et all: "Isotope effect of 13C enriched testosterone on human cells" published on Feb. 16, 2022: https://www.spandidos-publications.com/10.3892/wasj.2022.144.

Karolinska Institutet et all: "Ultralight ultrafast enzymes: Isotopes more powerful than previously thought" published on Dec. 4, 2023: https://phys.org/news/2023-12-ultralight-ultrafast-enzymes-isotopes-powerful.html.

(Continued)

*Primary Examiner* — Shirley V Gembeh

(74) *Attorney, Agent, or Firm* — Liang & Hennessey LLP; Stanley D. Liang

(57) ABSTRACT

A method for treating hematologic malignancies comprises administration of a composition inclusive of $^{64}Zn_e$(Asp) in a therapeutically effective amount. Such administration may be via intravenous injection and/or infusion and may be once a day or more than once a day. Other identified compounds may be bound to $^{64}Zn_e$ replacing L-Aspartate (Asp), provided that the resulting molecular weight does not exceed 700 Da and the resulting compound nanoparticles are less than 50.5 nm in size. The composition is suitable for intravenous injection and/or infusion.

3 Claims, 6 Drawing Sheets

(56) References Cited

OTHER PUBLICATIONS

Guillin, Olivia et all: "Zinc Uptake by HIV-1 Viral Particles: An Isotopic Study" published on Oct. 16, 2023: https://www.mdpi.com/1422-0067/24/20/15274.
Cheng, Yunqi et all: "Aberrance of Zinc Metalloenzymes-Induced Human Diseases and Its Potential Mechanisms" published on Dec. 13, 2021: https://pmc.ncbi.nlm.nih.gov/articles/PMC8707169/.
Costa, Maria et all: "Zinc: From Biological Functions to Therapeutic Potential" published on Mar. 2, 2023: https://pmc.ncbi.nlm.nih.gov/articles/PMC10003636/.
Bendellaa, Mohamed et all: "Roles of zinc in cancers: From altered metabolism to therapeutic applications" published on Aug. 23, 2023: https://onlinelibrary.wiley.com/doi/10.1002/ijc.34679.
Wang, Jie et all: "Zinc dysregulation in cancers and its potential as a therapeutic target" published on Aug. 15, 2020: https://pmc.ncbi.nlm.nih.gov/articles/PMC7476080/.
Narayan, Sugandha et all "Zinc dampens antitumor immunity by promoting Foxp3+ regulatory T cells" published on Aug. 24, 2024: https://www.frontiersin.org/journals/immunology/articles/10.3389/fimmu.2024. 1389387/full.
Buj, Raquel et all: "CDKN2ALow cancer cells outcompete macrophages for microenvironmental zinc to drive immunotherapy resistance" published in Bio Rx IV on Feb. 8, 2025, https://www.biorxiv.org/content/10.1101/2025.02.08.637227v2.full.
Zhou, Xiao-Hong et all: "Targeting phosphatidylserine in tumor cell membranes with a zinc-containing molecule to efficiently combat tumor metastasis" published in Journal of Nanobiotechnology on May 20, 2025: https://pmc.ncbi.nlm.nih.gov/articles/PMC12090580/.
Khalaji, Amirreza et all: "Don't eat me/eat me signals as a novel strategy in cancer immunotherapy" published in Heliyon on Sep. 29, 2023: https://pmc.ncbi.nlm.nih.gov/articles/PMC10562801/.
Xue, Jing et all: "Chloroquine Is a Zinc lonophore" published on Oct. 1, 2014: https://pmc.ncbi.nlm.nih.gov/articles/PMC4182877/.
Ekinci, Ilksen Berfin et all: "Ionophore Toxicity in Animals: A Review of Clinical and Molecular Aspects" published on Jan. 15, 2023: https://pmc.ncbi.nlm.nih.gov/articles/PMC9863538/.
Buchl, Anette et all: "Re-partitioning of Cu and Zn isotopes by modified protein expression" published on Oct. 10, 2008: https://pmc.ncbi.nlm.nih.gov/articles/PMC2570658/.
Burián, Z et all: "Selective Inhibition of HIF1a Expression by ZnSO4 Has Antitumoral Effects in Human Melanoma" published on Apr. 26, 2020: https://pubmed.ncbi.nlm.nih.gov/30613921/.
U.S. Appl. No. 19/076,021, filed Mar. 11, 2024.
U.S. Appl. No. 19/068,709, filed Mar. 3, 2025.
Paredes, Eduardo et all: "Impact of uranium uptake on isotopic fractionation and endogenous element homeostasis in human neuron-like cells" published on Nov. 21, 2018: https://pmc.ncbi.nlm.nih.gov/articles/PMC6249223/.

* cited by examiner

L1210 Leukemia Model
Cytotoxic Effect of KLS-1

A. L1210 Control

Experimental animals on Day 14 after KLS-1 injection into tumor

L1210 Leukemia Model
Cytotoxic Effect of KLS-1

B. L1210 + $^{64}Zn_e$(Asp)

Experimental animals on Day 14 after KLS-1 injection into tumor

| Type of experiment | Animals | Doses of $Zn^{64}$ Aspartate | Proteins | | | | | | |
|---|---|---|---|---|---|---|---|---|---|
| | | | Bcl-2 | Bax | p53 | pro-MMP-2 | pro-MMP-9 | MMP-2 | MMP-9 |
| in vivo | $BDF_1$ male mice | 13.9 mg/kg | increased expression by 3.4 times | increase in the expression by 5.5 times | increased expression of p53 (Y-5 clone and DO-7 clone by 7.5 and by 6.5 times, respectively | activity decreased by 53.9% | activity decreased by 50% | activity decreased by 29.1% | no effect |
| | | 27.81 mg/kg | increased expression by 3.3 times | increased expression by 7.8 times | increased expression of p53 (Y-5 clone and DO-7 clone by 12.4 times and 9-fold, respectively | activity decreased by 65.3% | activity decreased by 72.2% | activity decreased by 40.5% | activity decreased by 32.2% |

FIG. 6

PHARMACEUTICAL COMPOSITION AND METHOD OF TREATING HEMATOLOGIC MALIGNANCIES

FIELD

This disclosure relates to compositions and methods for treating a group of malignancies that affect the production and function of blood cells in a subject.

BACKGROUND

Blood cancers (also known as hematologic malignancies) are a group of malignancies affecting the production and function of blood cells. These cancers typically originate in the bone marrow, where blood cells are produced. The three main types of blood cancers are leukemia, lymphoma, and myeloma.

Leukemia is a cancer of the blood and bone marrow, characterized by the rapid production of abnormal white blood cells, which are crucial for fighting infections. There are four main types of leukemia: Acute Lymphoblastic Leukemia (ALL), Acute Myeloid Leukemia (AML), Chronic Lymphocytic Leukemia (CLL), and Chronic Myeloid Leukemia (CML). Acute leukemias progress rapidly and require immediate treatment, while chronic leukemias develop more slowly.

Lymphoma affects the lymphatic system, which is part of the body's immune system. The two main types of lymphoma are Hodgkin Lymphoma (HL) and Non-Hodgkin Lymphoma (NHL).

Myeloma is a cancer of plasma cells, which are white blood cells that produce antibodies. Multiple myeloma is the most common form, affecting more than 90% of myeloma patients.

Based on the latest data from the American Cancer Society's Cancer Statistics for 2025, blood cancers account for approximately 9.4% of all new cancer cases in the United States. An estimated 187,740 new cases of leukemia, lymphoma, and myeloma are expected to be diagnosed in the U.S. in 2024. An estimated over two million new blood cancer cases projected to be diagnosed in the U.S. in 2025. The overall five-year relative survival rate for all types of leukemia is ~67%. For lymphoma, the five-year relative survival rate is about ~74% for non-Hodgkin lymphoma and ~89% for Hodgkin lymphoma.

Yet, the treatment options for hematologic malignancies are still limited.

SUMMARY

In one aspect, this disclosure provides a pharmaceutical composition including a therapeutically effective amount of $^{64}Zn_e$ (Asp), wherein from 0.4 μg/kg patient weight to 1.682 g/kg patient weight of $^{64}Zn_e$ is administered to patient and wherein the $^{64}Zn_e$ is at least 90% $^{64}Zn$.

In another aspect, this disclosure provides a method of suppressing leukemia, lymphoma, and myeloma malignancy in a patient in need thereof including administering a pharmaceutical composition including a therapeutically effective amount of $^{64}Zn_e$ to said patient, wherein from about 0.4 μg/kg of patient weight to about 1.682 g/kg of patient weight of $^{64}Zn_e$ is administered to said patient and wherein the $^{64}Zn_e$ is at least 90% $^{64}Zn$.

BRIEF DESCRIPTION OF DRAWINGS

FIG. 6 illustrates data relating to dose dependent effect in L1210 leukemia mouse models after treatment with $^{64}Zn_e$ (Asp).

DETAILED DESCRIPTION

Figure 1:
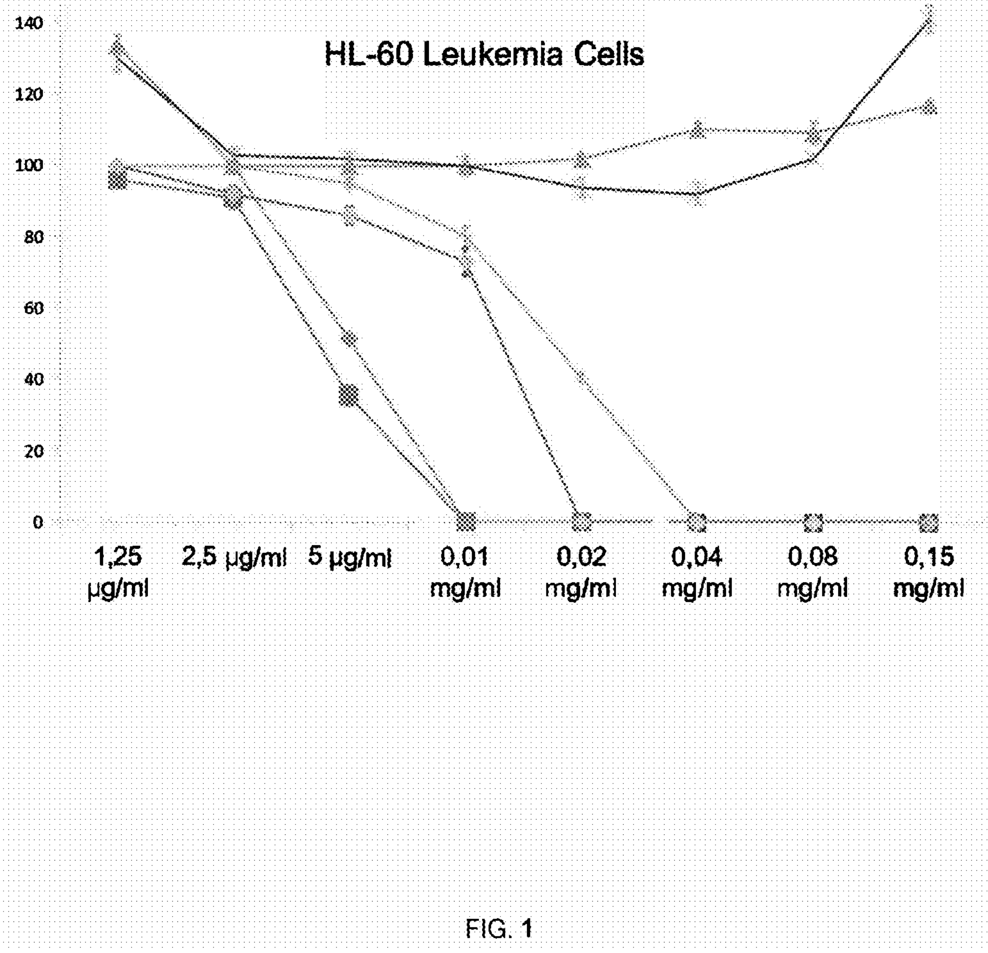
FIG. 1 illustrates data on cytotoxic and cytostatic action of $^{64}Zn_e$ comprising 2 molecules of aspartic acid/atom of zinc (written in shorthand herein as "$^{64}Zn_e$(Asp)" in experimental human leukemia cells (HL-60 cell line).

As used herein, the word "a" or "plurality" before a noun represents one or more of the particular noun.

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

All ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9. All ranges disclosed herein are also to be considered to include the end points of the range, unless expressly stated otherwise. For example, a range of "between 5 and 10" or "5 to 10" or "5-10" should be considered to include the end points 5 and 10.

The feature or features of one embodiment may generally be applied to other embodiments, even though not specifically described or illustrated in such other embodiments, unless expressly prohibited by this disclosure or the nature of the relevant embodiments. Likewise, compositions and methods described herein can include any combination of features and/or steps described herein not inconsistent with the objectives of the present disclosure. Numerous modifications and/or adaptations of the compositions and methods described herein will be readily apparent to those skilled in the art without departing from the present subject matter.

Unless otherwise defined, all technical and scientific terms used herein shall have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

As used herein, the term "chemical element" refers to any substance that cannot be decomposed into simpler substances by chemical processes. Elements are the fundamental materials of which all matter is composed.

The term "isotope" refers to a variant of an atom of a chemical element that differs by the number of neutrons in its nucleus and has a different atomic mass. According to the proton-neutron model developed by D. I. Ivanenko and W. Heisenberg (1932), atoms of all chemical elements consist of three types of elementary particles: positively charged protons, negatively charged electrons, and neutrons that have no charge. The number of protons p in the nucleus determines the atomic number Z of the chemical element in Mendeleev's periodic table. The proton and the neutron, which have a common name—nucleons—have almost identical weight. The mass of the neutron (1.00866 amu) is somewhat greater than the proton mass (1.00727 amu). The electron mass is much smaller than that of the nucleons (for example, the proton-to-electron mass ratio is 1836.13). Therefore, the mass of the atom is concentrated in its nucleus. Hence, the mass number of the atom A is connected with the atomic number by a simple relation $A=p+n=Z+n$, where n is the number of neutrons in the nucleus of an atom. The number of protons in the nucleus of an atom uniquely determines the position of an element in the periodic table of the elements. Furthermore, the number of protons determines the number of electrons present in a neutral atom thus determining the chemical properties of this atom. However, atoms with the same atomic number Z (and hence the number of protons p) may have different neutron numbers n. Thus, atoms with different atomic mass numbers may occupy the same position on the periodic table. Chemical elements having the same atomic number but a different atomic mass are known as isotopes.

Stable isotopes are a known matter. Although radioactive isotopes have been used in medicine for diagnostics and radiation therapies, the use of enriched stable isotopes has been limited to the applications in diagnostics, clinical pharmacology, and metabolic studies, all of which have used stable isotopes in their naturally abundant ratios. In diagnostics, stable isotopes have been used as tracers for dynamically assessing in vivo metabolism. In research, stable isotopes have been used in evaluating bioavailability and the release profile of drug products and drug delivery systems. In the assessment of drug pharmacology, stable isotopes have been used for the determination of a drug's pharmacokinetic profile, mechanism of action, and potential toxicity or adverse effects. In precision medicine, stable isotopes have recently started to be used monitoring drug treatment effects and conducting clinical toxicology studies. In nutrition, stable isotopes have been used to assess body composition, energy expenditure, protein turnover, food safety and metabolic profiles. However, all of these prior art techniques and technologies have used stable isotopes in their naturally occurring isotopic ratios.

The term "natural abundance" of an isotope refers to the fraction of the total amount of the corresponding element that the isotope represents, on a mole-fraction basis (that is, not, for example, on a mass basis). For example, $^{64}Zn$ has a natural abundance fraction of 48.63%, meaning that 48.63% of Zn atoms on earth are the isotope $^{64}Zn$. When a composition is "enriched" for a certain isotope, the abundance of the isotope in the composition is greater than the isotope's natural abundance. For $^{64}Zn$, a composition in which $^{64}Zn$ constitutes more than 48.63% of the total Zn in the composition, on a mole-fraction basis, would be "enriched" for $^{64}Zn$. As used herein, a subscript "e" following a light isotope chemical symbol or element name indicates that the designated element is enriched for that isotope. For example, $^{64}Zn$ refers to the light isotope zinc-64, whereas $^{64}Zn_e$ refers to zinc that is enriched for zinc-64. Thus, "$^{64}Zn_e$ aspartate," for example, refers to zinc aspartate in which the zinc is enriched for zinc-64.

The term "relative isotopic fraction" refers to a measure of the proportion of one isotope of a chemical element relative to another isotope of the sample of the same element, typically expressed in comparison to a standard reference. For example, the isotopic fraction of $^{64}Zn$ atoms of naturally occurring zinc is 48.6%.

The term "enriched" refers to the process of increasing the proportional fraction of a specific isotope within a mixture of isotopes. The enrichment process exploits the differences in physical and/or chemical properties between isotopes of the same element to separate and concentrate one isotope from the others. The term "isotopically modified" refers to the process of enriching an identified isotope. Hence, terms "enrichment" and "isotopic modification" essentially refer to the same concept. Isotope enrichment is also a known process of isotopic modification that refers to increasing the fraction of a specific isotope in a mixture of isotopes in a chemical element. An enrichment of light isotopes automatically results in a depletion of heavy isotopes of the same chemical element, and vice versa. The enriched stable isotopes of hydrogen (H), carbon (C), nitrogen (N), and oxygen (O) in both medicine and pharmaceutical applications have been used by the prior art. These enriched isotopes were used for various purposes, including drug development. For instance, isotopes $^{13}C$ and $^{15}N$ have been used in clinical medicine and biological studies. These isotopes are particularly valuable in the development of diagnostic tests, such as the $^{13}C$ urea breath test for detecting *Helicobacter pylori* infections. Also, the chemical compounds labeled with highly enriched $^{13}C$ are used in breath tests for diagnosing liver and intestine diseases. Stable isotopes $^{2}H$, $^{3}H$, $^{13}C$, $^{15}N$, and $^{18}O$ are heavy stable isotopes.

The term "therapeutic efficacy" refers to the ability of a medical intervention, such as a pharmaceutical composition or treatment method, to produce a beneficial effect under ideal and controlled circumstances. It is a critical concept in pharmacology and medicine, used to evaluate the potential of new treatments.

The terms "effective amount," "prophylactically effective amount," or "therapeutically effective amount" refers to an amount of an agent or composition that provides a beneficial effect or favorable result to a subject, or alternatively, an amount of an agent or composition that exhibits the desired in vivo or in vitro activity. That result can be reduction, amelioration, palliation, lessening, delaying, and/or alleviation of one or more of the signs, symptoms, or causes of a disease, disorder or condition in a patient/subject, or any other desired alteration of a biological system. An effective amount can be administered in one or more administrations. "Effective amount," "prophylactically effective amount," or "therapeutically effective amount" can refer to an amount of an agent or composition that provides a biological, therapeutic, and/or prophylactic result.

For any composition, an effective amount can be first estimated either in accordance with cell culture assays or using animal models, typically mice, rats, guinea pigs, rabbits, dogs or pigs. An animal model may be used to determine an appropriate concentration range and route of administration. Such information can then be used to determine appropriate doses and routes of administration for humans. When calculating a human equivalent dose, it is recommended to use a conversion table given in the Guidance for Industry and the Reviewers document (2002, US Food and Drug Administration, Rockville, MD, USA). An effective daily dose is generally 0.01 mg/kg patient weight to 2000 mg/kg patient weight of an active agent, preferably 0.05 mg/kg patient weight to 500 mg/kg patient weight of an active agent. An exact effective dose will depend on the severity of the disease, patient's general state of health, age, body weight and sex, nutrition, time and frequency of administration, combination(s) of medicines, response sensitivity and tolerance/response to administration and other factors that will be taken into account by a person skilled in the art when determining the dosage and route of administration for a particular patient based on his/her knowledge of the art. Such dose may be determined by conducting routine experiments and at the physician's discretion. Effective doses will also vary depending on the possibility of their combined use with other therapeutic procedures, such as the use of other agents.

The term "nascent form" refers to an isotope that is freshly formed, meaning it has just been created and is in its most reactive state, often with a higher potential for chemical reactions due to its immediate availability and lack of interaction with other molecules; essentially, it's an isotope in the moment of its formation, before it has had a chance to stabilize or bond with anything else.

The term "colloidal form" refers to a specific isotope of an element that exists as nanoparticles suspended in a liquid, forming a colloid; essentially, the isotope is dispersed in a medium as very small, stable particles that are too small to settle out readily, creating a uniform mixture.

The term "elemental form" refers to a specific variant of a chemical element, where most atoms of that element have the same number of protons and the same number of neutrons, essentially meaning they are the same isotopes of the same element, existing in their pure state as a chemical element.

The term "atomic form" refers to a single atom of that element.

The term "molecule" is known in the art. Briefly, it refers to an electrically neutral group of two or more atoms held together by chemical bonds. Molecules form the smallest identifiable unit of a chemical compound that retains the composition and chemical properties of that compound. Examples include carbohydrates, lipids, and ribonucleic acid.

The term "treating" as used herein with respect to a medical condition such as any type or kind of leukemia, lymphoma, or myeloma refers to lessening severity and/or consequences of the condition, slowing progression of the condition, reversing pathology of the condition, and/or curing the condition.

The term "preventing" as used herein with respect to a medical condition such as either leukemia, lymphoma, or myeloma refers to preventing the development of metastasis, diminishing the severity of metastasis, lessening consequences of metastasis, and/or slowing progression of metastasis.

The terms "patient" and "subject" are interchangeable terms and may refer to a human patient/subject, a dog, a cat, a non-human primate, and other mammals.

The term "leukemia" refers to any leukemia, including Acute Lymphoblastic Leukemia (ALL), Acute Myeloid Leukemia (AML), Chronic Lymphocytic Leukemia (CLL), and Chronic Myeloid Leukemia (CML), whether made collectively or individually, directly or indirectly.

The term "lymphoma" refers to any lymphoma, including Hodgkin Lymphoma (HL) and all subtypes of Non-Hodgkin Lymphoma (NHL).

The term "myeloma" refers to any myeloma, including multiple myeloma, light chain myeloma (a.k.a. Bence Jones myeloma), non-secretory myeloma, hyperdiploid myeloma, non-hyperdiploid myeloma, and smoldering multiple myeloma (SMM).

The term "amino acid" refers to organic compounds that consist of a central carbon atom (α-carbon), an amino group (—$NH_2$), a carboxyl group (—COOH), and a unique side chain (R group). Amino acids combine to form proteins through peptide bonds, creating long chains that fold into complex three-dimensional structures. Furthermore, the term "essential amino acids" refer to a group of amino acids that cannot be synthesized by the human body and must be obtained through diet.

The initial antitumor effect of essential amino acids is a known matter. However, administering leucine, isoleucine, phenylalanine, or threonine alone is not sufficient for an effective blood cancer treatment. The effects of these amino acids on blood cancers is complex and context-dependent. Leucine may promote tumor progression in some cases (Beaudry et al., Nutrients. 2022 Jul. 9; 14 (14): 2824. doi: 10.3390/nu14142824). Phenylalanine's role in blood cancers is not well-established; however, increased blood concentrations of phenylalanine are common in patients with cancer, but the reason for this is unclear (Neurauter et al., Cancer Lett. 2008 Dec. 8; 272 (1): 141-7. doi: 10.1016/j.canlet.2008.07.002. Epub 2008 Aug. 12). Threonine deaminase, which depletes threonine, showed some anti-leukemic effects in vitro, which is different from and opposite to administering threonine (Greenfield et al., Cancer Res (1977) 37 (8_Part_1): 2523-2529) Furthermore, studies show that administering the majority of amino acids alone (both essential and non-essential) promotes cancer progression.

Zinc also plays a complex and sometimes contradictory role through its effects on the Bcl-2 and Bax pathways. While it can induce apoptosis and inhibit tumor growth in some cases, elevated zinc levels have also been associated with increased aggressiveness of cancers.

This disclosure provides combining certain amino acids with isotopically modified $^{64}Zn_e$, which will allow for enhanced therapeutic effect against blood cancer cells through A20 and PPARα pathways, which play complex and sometimes contradictory roles in blood cancers, influencing tumor progression, treatment response, and immune regulation.

Zinc and isoleucine may affect different but complementary signaling pathways involved in cancer cell survival and proliferation. Isoleucine may also enhance the cellular uptake of $^{64}Zn_e$, furthering the enhancement onto intracellular effects against cancer cells.

A20 acts as a tumor suppressor in B-cell lymphomas, with biallelic inactivation observed in one-third of ABC-DLBCL cases (Mandelbaum et al., Blood (2010) 116 (21): 148). A20 regulates BV sensitivity likely through its ability to mediate cellular pathways required for directing MMAE cytotoxicity (Wei et al., Clin Cancer Res (2020) 26 (15): 4093-4106). Studies also show that A20 haploinsufficiency can disturb immune homeostasis and drive the expansion of distinct lymphocytes, potentially contributing to lymphoma development (Schultheiß et al., Science Advances 21 Aug. 2024 Vol 10, Issue 34 DOI: 10.1126/sciadv.adl3975). PPARα, a nuclear receptor involved in lipid metabolism and inflammation, also exhibits complex effects in blood cancers. On one side, PPARα has been suggested as a therapeutic target for chronic lymphocytic leukemia. PPARα mediates glucocorticoid resistance and promotes CLL progression (Xiang et al., PPAR Res. 2023 Jun. 26; 2023:8456833.) On another side, in Philadelphia chromosome-positive lymphocytic leukemia cell lines, PPARγ ligands (which can cross-activate PPARα) inhibited cell proliferation and induced apoptosis (Liu et al., Blood (2006) 107 (9): 3683-3692).

Both A20 and PPARα can influence apoptotic pathways in cancer cells, though their effects may vary depending on the cellular context. The novelty claimed in this patent application is in the use of isotopically modified $^{64}Zn_e$, which will allow for enhanced antitumor effect against blood cancer cells through A20 and PPARα pathways.

The term "carotene" refers to hydrocarbons containing only carbon and hydrogen atoms.

The term "xanthophyll" refers to hydrocarbons containing oxygen atoms in addition to carbon and hydrogen atoms.

Carotenoids, both carotene and xanthophyll, belong to a class of organic compounds that are naturally existent in plants. Their antitumor potential is also a known matter. However, it is also known that carotene and xanthophyll may influence cell cycle progression in blood cancer cells.

Zinc plays a complex and sometimes contradictory role through its effects on the Bcl-2 and Bax pathways. While it can induce apoptosis and inhibit tumor growth in some cases, elevated zinc levels have also been associated with increased aggressiveness in certain cancers.

In certain embodiments, this disclosure provides combining certain carotenoids with isotopically modified zinc ($^{64}Zn_e$), which allows for enhanced therapeutic effect against blood cancer cells primarily through increasing the Bax/Bcl-2 ratio, creating a pro-apoptotic cellular environment.

Isotopically natural chemical elements have been historically used for making various organic molecules and pharmaceutical compositions. Enriched medical radioisotopes have been used in pharmaceutical industry since the early 1930s, playing an important role in advancing nuclear medicine and enabling the development of more effective therapeutic radiopharmaceuticals. One of the earliest recorded uses was by John Lawrence, who in 1936 used phosphorus-32, a radioactive isotope, to treat leukemia. This marked the first clinical therapeutic application of an artificially enriched radionuclide.

The development of organic compounds has traditionally relied on naturally occurring isotopes of chemical elements. The use of enriched stable isotopes in pharmaceuticals as part of organic molecules commenced with the discovery of deuterium by Harold Urey in 1932. For the first several decades, the focus was on understanding biological and chemical processes, leveraging the ability of stable isotopes like deuterium and tritium to be detected through mass spectrometry and radioactivity measurements, respectively. Despite tritium being a radioactive isotope, its long half-life and the stable nature of deuterium allowed for safe handling and application in various biomedical areas. The concept of deuteration (substituting a hydrogen atom with deuterium atom) emerged as a significant advancement in drug discovery in the following decades. This innovative approach emerged with the development of deutetrabenazine (U.S. Pat. No. 8,524,733) approved by U.S. FDA in 2017 and deucravacitinib (WO 2018/183656) approved in 2022. Both deutetrabenazine and deucravacitinib use isotopically modified hydrogen 1H. These breakthroughs marked the beginning of a new era in pharmaceutical design, focusing on the isotopic modification of stable isotopes.

Zinc aspartate is a form of zinc compound that combines isotopically natural zinc with aspartic acid. It is commonly used to treat zinc deficiency and may offer several potential health benefits. Isotopically natural zinc has five stable isotopes in the following percentages: $^{64}Zn$ (48.63%), $^{66}Zn$ (27.90%), $^{67}Zn$ (4.10%), $^{68}Zn$ (18.75%), and $^{70}Zn$ (0.62%). The $^{64}Zn_e$ aspartate disclosed herein is isotopically modified by enrichment of $^{64}Zn$ atoms to at least 90%, and, in certain embodiments, enrichment of aspartate for the L-enantiomer for at least 90%.

In some embodiments, $^{64}Zn_e$ (Asp), or zinc aspartate, has a chemical formula —$(C_4H_5O_4N)_2{}^{64}Zn_e$, with 2 aspartic acid molecules.

The typical dosage of isotopically natural zinc aspartate ranges from 10-30 mg of elemental zinc per day regardless of the person's body weight. The therapeutically or prophylactically effective dose of isotopically modified $^{64}Zn_e$(Asp) disclosed herein ranges from 0.4 μg/kg patient weight per day to 1.682 g per kg patient weight per day. The isotopically natural zinc aspartate (not enriched for $^{64}Zn$) used in the prior art is administered orally.

In some embodiments, the isotopically modified $^{64}Zn_e$ (Asp) is administered intravenously. In some embodiments, the composition is administered parenterally. In some embodiments, the composition is administered by infusion. In some embodiments, the composition is administered parenterally by infusion.

Recently, a number of works have demonstrated that an isotopic composition of tissues and organs may serve as a diagnostic marker. Furthermore, studies demonstrate that blood cancer cells exhibit isotopic fractionation of zinc and copper. A 2020 study on hematological malignancy (HM) patients (Hastuti et al., nature research Scientific Reports| (2020) 10:16389|https://doi.org/10.1038/s41598-020-71764-7) examined the levels of isotopically natural copper and zinc in blood as diagnostic biomarkers and found significant differences in plasma Cu and Zn isotope ratios compared to matched controls. The study showed that the group of patients with decreased $\delta^{65}Cu$ and increased $\delta^{66}Zn$ values showed significantly poorer survival from the early phase (HR 3.9; P=0.001.) The $\delta^{65}Cu$ notation represents the relative difference in the 65Cu/63Cu ratio between a sample and a standard, typically expressed in parts per thousand (‰) Hence, a decreased $\delta^{65}Cu$ value refers to the increased 63Cu fraction. The same is true for zinc: an increased $\delta^{66}Zn$ value refers to the decreased $^{64}Zn$ fraction in blood cells. In this 2020 study, both increased $^{63}Cu$ and decreased $^{64}Zn$ values showed significant mortality hazard ratios (HRs) in HM. Further, certain patents and patent applications discuss the use of isotopically enriched compositions for therapeutic use. See, e.g., U.S. Pat. Nos. 9,861,659; 10,183,041, and 12,138,322.

$^{64}Zn_e$ acts as an isotope-selective modulator of Bax-associated pore formation in mitochondria, leading to cytochrome c release and caspase activation, increasing cellular levels of pro-apoptotic Bax protein and decreasing expression of anti-apoptotic Bcl-2 protein.

Carotenes can contribute to inducing apoptosis in cancer cells through multiple mechanisms in addition to antiproliferative effects and immunomodulation along with regulating antioxidant/pro-oxidant activities.

In certain embodiments, from 0.4 μg/kg of patient weight to 1.682 g/kg of patient weight of $^{64}Zn_e$ is administered to a patient in need thereof.

In one aspect, this disclosure provides a pharmaceutical composition to treat hematologic malignancies. The composition includes a therapeutically effective amount of $^{64}Zn_e$ (Asp), wherein from 0.4 μg/kg patient weight to 1.682 g/kg patient weight of $^{64}Zn_e$ is administered to a patient in need thereof and wherein the $^{64}Zn_e$ is at least 90% $^{64}Zn$. In some embodiments, the aspartate (Asp) is replaced by at least one of alanine (Ala), proline (Pro), tyrosine (Tyr), or phenylalanine (Phe), or a combination thereof, wherein the resulting molecule size is below 155.2 nm. In some embodiments, the aspartate is replaced by at least one of quercetin, apigenin, genistein, kaempferol, and chrysin, or a combination thereof, wherein the resulting molecule size is below 155.2 nm. In some embodiments, the aspartate is replaced by at least one of curcumin, epigallocatechin gallate, or resveratrol, or a combination thereof, wherein the resulting molecule size is below 155.2 nm. In some embodiments, the composition includes deuterium-depleted water. In some embodiments, the composition includes a carrier selected from the group consisting of polymeric micelles, metal organic framework, liposome, and a loaded platelet. In some embodiments, the $^{64}Zn_e$ (Asp) is enriched for the L-enantiomer to at least 90%.

In another aspect, this disclosure provides a method of suppressing leukemia, lymphoma, and myeloma malignancy in a patient in need thereof including administering a pharmaceutical composition including a therapeutically effective amount of $^{64}Zn_e$ to said patient, wherein from about 0.4 μg/kg of patient weight to about 1.682 g/kg of patient weight of $^{64}Zn_e$ is administered to said patient and wherein the $^{64}Zn_e$ is at least 90% $^{64}Zn$.

In some embodiments, the $^{64}Zn_e$ is in elemental, atomic, ionic, or nascent form. In some embodiments, the $^{64}Zn_e$ is in colloidal form. In some embodiments, the composition is in molecular form. In some embodiments, the composition is formulated into various dosage forms suitable for administration by injection or infusion and the composition has molecular weight of less than 699.9 Da. In some embodiments, the composition is administered by injection or infusion.

In another aspect, a method is provided for treatment of hematologic malignancies and for preventing the development of metastases of hematologic malignancies comprising intravenous administration to a patient of $^{64}Zn_e$ (Asp) composition containing 2 molecules of aspartic acid for each atom of $^{64}Zn$, at a therapeutically effective dose.

In certain embodiments, the composition of $^{64}Zn_e$ (Asp) is enriched for the L-enantiomer for at least 90% L-enantiomer. In other embodiments, the composition of $^{64}Zn_e$ (Asp) may be changed to a similar composition of $^{64}Zn_e$ (x) composition wherein x is an amino acid or a subclass or a variation of an amino acid bonded to $^{64}Zn_e$ as a replacement for aspartic acid and the $^{64}Zn_e$ concentration exceeds 80.4 μM.

In another aspect, the method is provided for treatment of hematologic malignancies and for preventing the development of metastases comprising intravenous administration to a patient of $^{64}Zn_e$ (–) composition including a pharmaceutical carrier. In one embodiment, the carrier is a polymeric micelle, metal organic framework, liposome or a loaded platelet. In another embodiment, the carrier is deuterium-depleted water.

In certain embodiments, the $^{64}Zn$-enriched zinc in $^{64}Zn_e$ (Asp) is at least 90% $^{64}Zn$ (that is, the (–) is Asp), the nanoparticle carriers are less than 55.2 nm in size, and the composition has molecular weight of less than 499.9 Da. As used herein, unless otherwise indicated, X % $^{64}Zn$ means that, out of 100 zinc atoms, X is $^{64}Zn$. For example, in zinc, that is 90% $^{64}Zn$, 90% of the atoms are $^{64}Zn$. Unless otherwise indicated, the term "$^{64}Zn$." is used herein as shorthand for "$^{64}Zn$-enriched zinc".

In some embodiments, the hematologic malignancy is Acute Lymphoblastic Leukemia (ALL), Acute Myeloid Leukemia (AML), Chronic Lymphocytic Leukemia (CLL), or Chronic Myeloid Leukemia (CML). In some embodiments, the hematologic malignancy is Hodgkin Lymphoma (HL) and all subtypes of Non-Hodgkin Lymphoma (NHL). In some embodiments, the hematologic malignancy is multiple myeloma, light chain myeloma (a.k.a. Bence Jones myeloma), non-secretory myeloma, hyperdiploid myeloma, non-hyperdiploid myeloma, and smoldering multiple myeloma (SMM).

The terms "quercetin, apigenin, genistein, kaempferol, and chrysin" collectively refer to flavonoids, which is a class of polyphenolic secondary metabolites found naturally in plants. They have a characteristic 15-carbon skeleton structure consisting of two phenyl rings (A and B) connected by a heterocyclic pyrene ring (C), typically abbreviated as $C_6$-$C_3$-$C_6$. These flavonoids is a known matter, which features an initial indication of antitumor potential. The combination of one or more of these flavonoids with the isotopically modified zinc ($^{64}Zn_e$), allow for enhanced therapeutic effect against blood cancer cells through targeting Bruton's tyrosine kinase (BTK) activation in blood cancer cells. In some embodiments, (–) is a flavonoid. Flavonoid includes, for example, quercetin, apigenin, genistein, kaempferol, and chrysin.

In some embodiments, the aspartate is replaced by one or more of quercetin, apigenin, genistein, kaempferol, and chrysin, wherein the resulting molecule size is below 700 Da. In some embodiments, the aspartate is replaced by one or more of curcumin, epigallocatechin gallate, or resveratrol, wherein the resulting molecule size is below 700 Da. In some embodiments, the composition includes deuterium-depleted water. In some embodiments, the composition includes a carrier selected from an ionophore, metallophore, polymeric micelle, metal organic framework, liposome, or a loaded platelet.

In some embodiments, the (Asp) is replaced by indole-3-carbinol or isoleucine, wherein the isoleucine is enriched for the L-enantiomer to at least 90%, and wherein the resulting molecule size is below 700 Da.

BTK activation is a key driver in the progression of many B-cell malignancies, influencing cancer cell survival, proliferation, and interactions with the microenvironment. This central role has made BTK an important target for therapeutic intervention in blood cancers. This patent application teaches new understanding of the role zinc isotopes may play in BTK activation and inhibition, which could lead to the development of more effective and selective BTK inhibitors for treating various B cell malignancies.

BTK is a crucial component of the B-cell receptor (BCR) signaling pathway. BTK acts downstream of the BCR, transmitting signals that promote B-cell survival, proliferation, and migration. On one side, zinc is essential for BTK function due to its TH domain having a zinc finger motif that is important for the protein activity and stability. Some BTK inhibitors (e.g. CGI-1746) have been shown to inhibit both auto- and trans-phosphorylation steps necessary for BTK enzyme activation, which may affect multiple pathways important for cell survival, proliferation, and migration, that in turn is necessary for healthy cellular functions. On another side, in many B-cell malignancies, BTK shows constitutive activity, leading to aberrant BCR signaling. This constant activation contributes to uncontrolled B-cell proliferation and survival. Chronic lymphocytic leukemia (CLL) cells also exhibit constitutive activation of the BCR signaling pathway, with BTK showing constant activity. The inhibition of BTK in primary human CLL cells promoted apoptosis of CLL cells. BTK activation is implicated in various other B-cell cancers, including mantle cell lymphoma, follicular lymphoma, and diffuse large B-cell lymphoma.

The critical role of BTK in blood cancer progression has led to the development of BTK inhibitors as targeted therapies. Ibrutinib, the first-in-class BTK inhibitor, has shown efficacy in treating various B-cell malignancies. Other BTK inhibitors, such as zanubrutinib, are also being developed and studied for their potential in treating blood cancers. None of these BTK inhibitors uses isotopically modified zinc in their formulations, however.

The term "indole-3-carbinol" refers to a bioactive phytochemical found abundantly in cruciferous vegetables and may be synthesized for use in organic compounds. Indole-3-carbinol exhibits anticarcinogenic properties across multiple cancer types by affecting cell cycle arrest, apoptosis, and inhibition of angiogenesis.

The term "isoleucine" refers to an essential amino acid that plays a crucial role in various bodily functions. It is one of the three branched-chain amino acids (BCAAs), along with leucine and valine.

The disclosed composition can be produced by methods employed in accordance with general practice in the pharmaceutical industry, such as, for example, the methods illustrated in Remington: The Science and Practice of Pharmacy (Pharmaceutical Press; 21 st revised ed. (2011) (hereinafter "Remington").

In some embodiments, the disclosed compositions comprise at least one pharmaceutically acceptable carriers or excipient. These include also include, for example, diluents, carriers, excipients, fillers, disintegrants, solubilizing agents, dispersing agents, preservatives, wetting agents, preservatives, stabilizers, buffering agents (e.g. phosphate, citrate, acetate, tartrate), suspending agents, emulsifiers, and penetration enhancing agents such as DMSO, as appropriate. The composition can also comprise suitable auxiliary substances, for example, solubilizing agents, dispersing agents, suspending agents and emulsifiers.

In certain embodiments, the composition further comprises suitable diluents, glidants, lubricants, acidulants, stabilizers, fillers, binders, plasticizers or release aids and other pharmaceutically acceptable excipients.

A complete description of pharmaceutically acceptable excipients can be found, for example, in Remington's Pharmaceutical Sciences (Mack Pub., Co., N.J. 1991) or other standard pharmaceutical science texts, such as the Handbook of Pharmaceutical Excipients (Shesky et al. eds., 8th ed. 2017).

EXAMPLES

For this invention to be better understood, the following examples are set forth. These examples are for purposes of illustration only and are not to be construed as limiting the scope of the invention in any manner.

Example 1. Cytotoxic/Cytostatic Effects of Zn Compounds on the HL-60 Cell Line Cells Studies to assess the in vitro effects of various doses of $^{64}Zn_e$ inclusive compounds on the viability and proliferation of blood cancer cells were performed.

HL-60 is a promyelocytic leukemia cell line. Collins S. J. The HL60 promyelocytic leukemia cell line: proliferation, differentiation and cellular oncogene expression. Blood. 1987, No 70: 1233. The HL-60 cell line was derived from peripheral blood lymphocytes obtained by leukapheresis of a 36-year-old Caucasian female with acute promyelocytic leukemia. The predominant cell population that has been preserved consists of neutrophil promyelocyte with prominent nuclear/cytoplasmic asynchrony. Approximately 10% of HL-60 cells spontaneously differentiate beyond the promyelocytic stage and the proportion of differentiated cells is markedly enhanced by polar planar compounds such as DMSO. Many other compounds, including butyrate, hypoxanthine, TPA, actinomycin D, and retinoic acids also induce differentiation. HL-60 cells lack specific markers for lymphoid cells but express surface receptors for the Fc fragments and complement system proteins. Cells exhibit phagocytic activity and responsiveness to chemotactic stimuli. Morphologically, the cells are lymphoblastoid. HL-60 cells form colonies in semi-solid media and produce subcutaneous myeloid tumors in nude mice. This cell line is used for experimental studies on cell differentiation.

The HL-60 cells were cultured and used in the experiments.

The results were evaluated using the MTT colorimetric assay or trypan blue dye exclusion assay.

The findings of the study show that according to the MTT assay $^{64}Zn_e$ aspartate and $^{64}Zn_e$ glutamate exhibit the highest activity against HL-60 cells among the zinc compounds (IC50 is 0.0000647 and 0.0000801 mol/L, respectively). At the same time, it should be noted that natural Zn aspartate and natural Zn glutamate did not exhibit any cytotoxic effects at concentrations≤2.34 mmol/L, moreover, an increase in the metabolic activity of tumor cells was observed in some cases, which may indicate their stimulation.

The data obtained in the trypan blue assay confirm stimulation of cell proliferation when the cells are exposed to the action of isotopically natural zinc compounds (zinc aspartate and zinc glutamate).

Given such significant differences in the cytotoxic/cytostatic activity of zinc compounds containing $^{64}Zn_e$ light isotope and the activity of isotopically natural zinc compounds, the cytotoxic effects on tumor cells are induced by $^{64}Zn_e$ light stable isotope present in their molecules rather than the cited amino acids. Such assumption is supported by the results of assessment of cytotoxic effects of aspartic and glutamic amino acids obtained in the MTT and trypan blue assays which indicate possible stimulation of growth of HL-60 tumor cells when exposed to the said amino acids at concentrations≤2.34 mmol/L. See FIG. 1.

$^{64}Zn_e$ sulfate and natural Zn sulfate had less pronounced effects as compared with $^{64}Zn_e$ aspartate and $^{64}Zn_e$ glutamate.

FIG. 1 illustrates data on cytotoxic and cytostatic action of $^{64}Zn_e$ comprising 2 molecules of aspartic acid/atom of zinc (written in shorthand herein as "$^{64}Zn_e$(Asp)" in experimental human leukemia cells (HL-60 cell line) by comparison to the cytotoxic and cytostatic action of isotopically natural zinc aspartate. The data shown in FIG. 1 illustrates that administering the isotopically natural compound, zinc aspartate, to lung cancer, HL-60 cells had short-lived cytotoxic effect. The isotopic modification by enrichment of light isotope $^{64}Zn$ has resulted in a new molecule, $^{64}Zn_e$ Aspartate, which had shown cytotoxic effect of HL-60 cells.

Example 2. Comparative Assessment of the In Vitro Activity of Zinc Compounds Against Cells of Mouse Tumor Model Strain of Leukemia The aim of this study was to assess the in vitro effects of different doses of experimental zinc compounds containing a stable light isotope of zinc ($^{64}Zn_e$) in the form of aspartate, citrate and sulfate, as well as natural Zn aspartate on the viability and proliferation of tumor cells.

The number of live cells was counted using the MTT assay (Sigma, USA) according to a standard procedure or by staining cells with trypan blue. In the case of MTT, the results were evaluated using a multi-well spectrophotometer at an excitation wavelength of 540 nm or with a hemocytometer in the case of staining cells with trypan blue.

Mouse leukemia L1210 cells are used in experiments to assess the antitumor activity of drugs intended for treating leukemia in both in vitro and in vivo models.

The L1210 cell strain was obtained in 1948 when it was induced in the spleen and lymph nodes of a DBA2 female mouse by dubbing its skin with methylcholanthrene. L1210 is transplanted in DBA2 female mice; the tumor takes in almost 100% of the laboratory animals. There is massive leukemia infiltration in the bone marrow, liver, spleen, lymph nodes, as well as the brain. Leukemia L1210 cells are atypical hemocytoblasts. Most of the tumor cells contain a large nucleus in which chromatin is collected in the form of a dense grid. The cytoplasm, having the form of a very narrow rim, is distinguished by an elevated basophilia. Multiple pinocytotic vacuoles are found in the cytoplasm. There are many mitoses. Law L. W., Dunn T. B., Boyle P. J. et al. Observation on the effect of a folic acid antagonist on transplantable lymphoid leukemias in mice//J. Natl. Cancer Inst.-1949.-v. 10.-P. 179-192.

It is known that L1210 strain is highly sensitive to folic acid antagonists (methotrexate, etc.) and less sensitive to purine and ethyleneimine antagonists. Chloroethylamine alkylating group of preparations, with the exception of cyclophosphan, suppress the development of leukemia to a lesser extent than antimetabolites. Goncharova S. A., Konovalova N. P., Lipchina L. P., Frankfurt O. S., Shvetsova V. N. Cellular cycle of transplantable leukemia L-1210//Oncol. Issues-1973.-V. 19, No 11.-P. 60-65.

The results demonstrate that $Zn^{64}$ aspartate was the most active against mouse leukemia L1210 cells and $Zn^{64}$ sulfate was the least active. See FIG. 2-FIG. 6.

Figure 2:
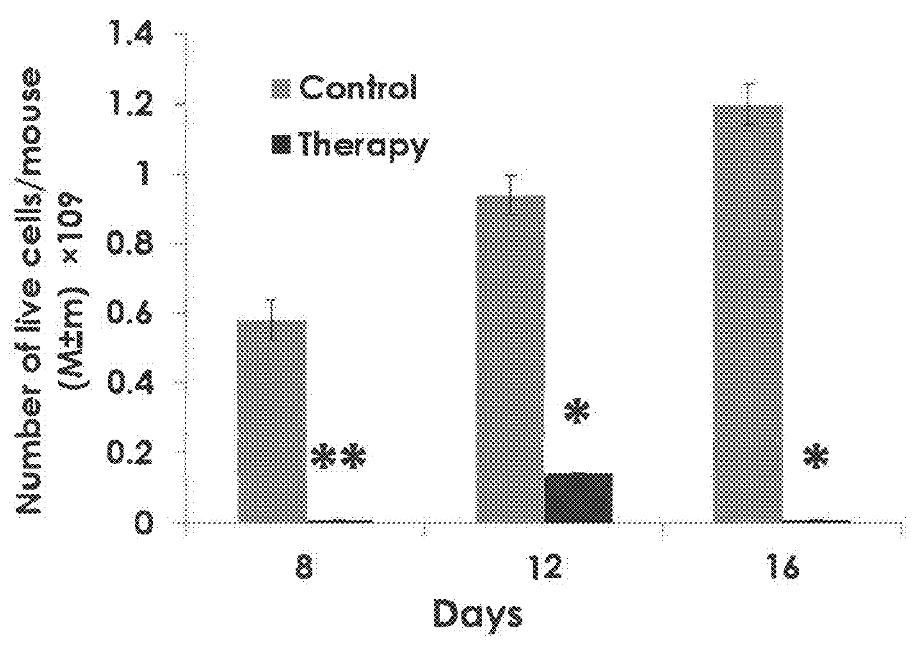
FIG. 2 illustrates data on the antitumor activity of $^{64}Zn_e$ (Asp) in L1210 leukemia mouse models by comparison to control.

FIG. 2 illustrates data on the antitumor activity of $^{64}Zn_e$ (Asp) in L1210 leukemia mouse models by comparison to control.

Figure 3:
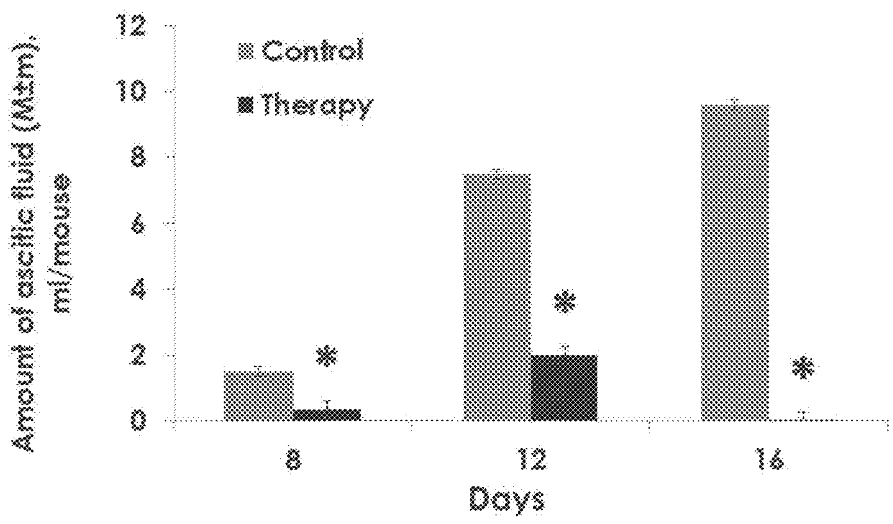
FIG. 3 illustrates data on the effect of $^{64}Zn_e$ (Asp) on the ascitic fluid in the abdominal cavity of L1210 mouse models by comparison to control.

FIG. 3 illustrates data on the effect of $^{64}Zn_e$ (Asp) on the ascitic fluid in the abdominal cavity of L1210 mouse models by comparison to control.

Figure 4:
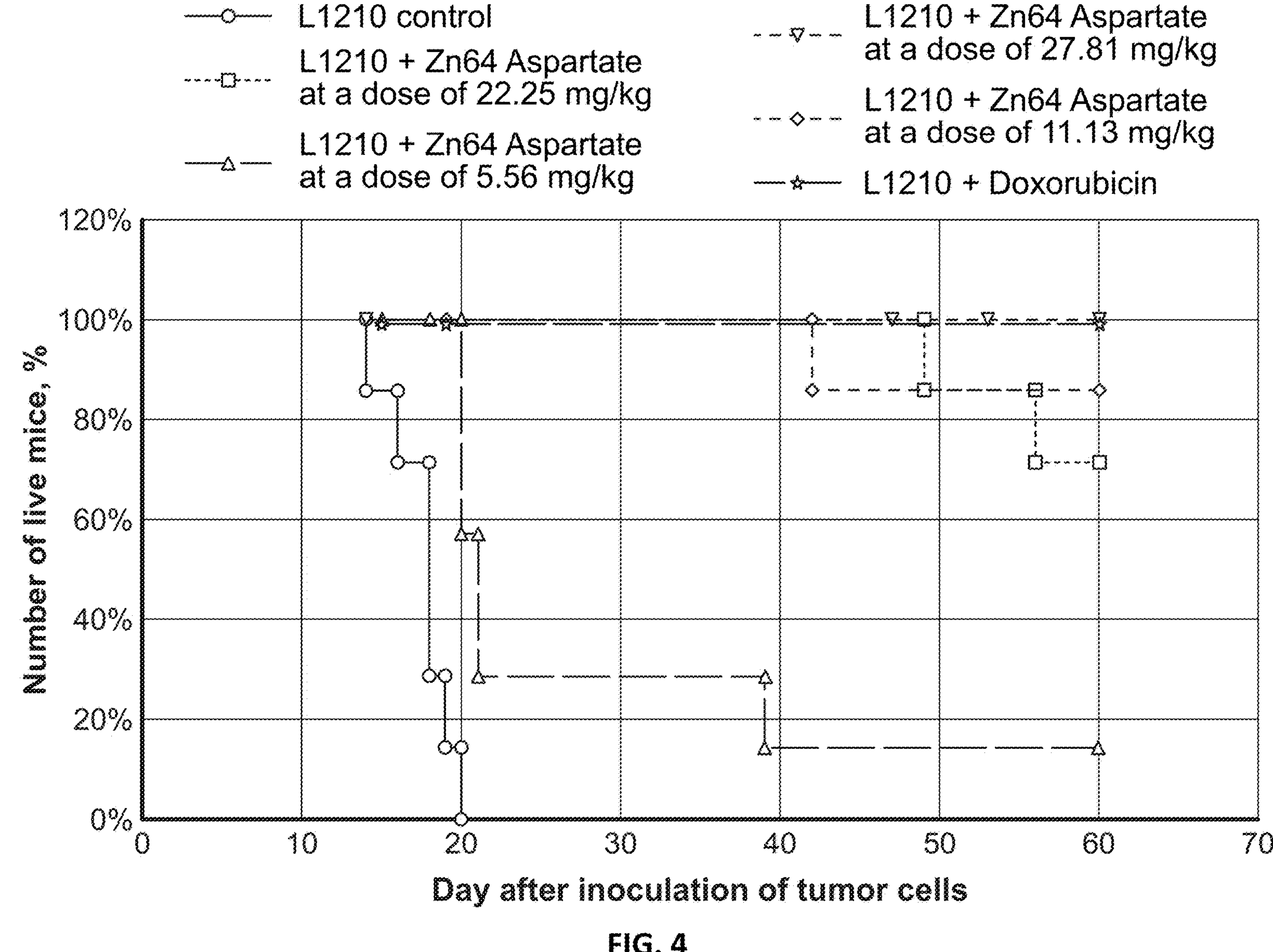
FIG. 4 illustrates data on dose dependent inhibition of tumor growth in L1210 leukemia mouse models after treatment with $^{64}Zn_e$ (Asp) by comparison to control.

FIG. 4 illustrates data on dose dependent inhibition of tumor growth in L1210 leukemia mouse models after treatment with $^{64}Zn_e$ (Asp) by comparison to control.

Figure 5A:
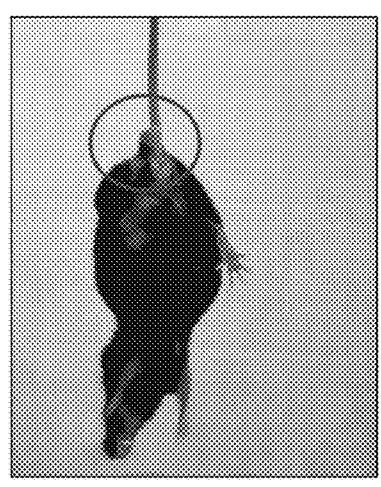
FIG. 5A and FIG. 5B illustrate antitumor effects in L1210 leukemia mouse models after treatment with $^{64}Zn_e$(Asp) (FIG. 5B) by comparison to control (FIG. 5A).
Figure 5B:
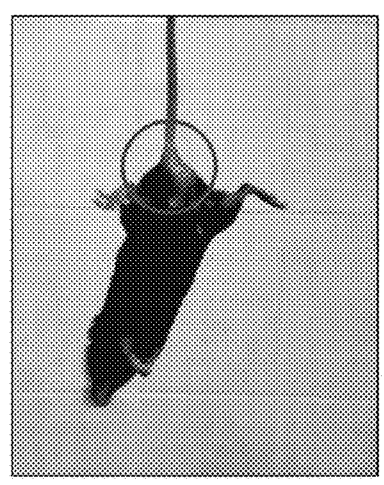

FIG. 5 illustrates antitumor effects in L1210 leukemia mouse models after treatment with $^{64}Zn_e$ (Asp) by comparison to control.

FIG. 6 illustrates data relating to dose dependent effect in L1210 leukemia mouse models after treatment with $^{64}Zn_e$ (Asp).

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the appended claims. Thus, while only certain features of the invention have been illustrated and described, many modifications and changes will occur to those skilled in the art. It is therefore to be understood that the appended claims are intended to cover all such modifications and changes as fall within the true spirit of the invention.

What is claimed is:

1. A pharmaceutical composition for suppressing leukemia, lymphoma, and myeloma malignancies including a therapeutically effective amount of $^{64}Zn_e$(Asp), wherein from 0.4 μg/kg patient weight to 1.682 g/kg patient weight of $^{64}Zn_e$ is administered to patient, wherein the $^{64}Zn_e$ is at least 90% $^{64}Zn$, and wherein aspartate is replaced by one or more of quercetin, apigenin, genistein, kaempferol, and chrysin, wherein the resulting molecule size is below 700 Da.

2. A pharmaceutical composition for suppressing leukemia, lymphoma, and myeloma malignancies including a therapeutically effective amount of and wherein aspartate is replaced by one or more $^{64}Zn_e$(Asp), wherein from 0.4 μg/kg patient weight to 1.682 g/kg patient weight of $^{64}Zn_e$ is administered to patient, wherein the $^{64}Zn_e$ is at least 90% $^{64}Zn$, and wherein aspartate is replaced by one or more of curcumin, epigallocatechin gallate, or resveratrol, wherein the resulting molecule size is below 700 Da.

3. A pharmaceutical composition for suppressing leukemia, lymphoma, and myeloma malignancies including a therapeutically effective amount of $^{64}Zn_e$ (Asp), wherein from 0.4 μg/kg patient weight to 1.682 g/kg patient weight of $^{64}Zn_e$ is administered to patient, wherein the $^{64}Zn_e$ is at least 90% $^{64}Zn$, and wherein the composition includes a carrier selected from an ionophore, metallophore, polymeric micelle, metal organic framework, liposome, or a loaded platelet.

* * * * *